United States Patent [19]

Pines et al.

[11] Patent Number: 5,605,887
[45] Date of Patent: *Feb. 25, 1997

[54] THERAPEUTIC FIBRINOGEN COMPOSITIONS

[75] Inventors: Eli Pines, Watchung, N.J.; William J. White, Wayne, Pa.

[73] Assignee: Fibratek, Inc., Pepper Pike, Ohio

[ * ] Notice: The term of this patent shall not extend beyond the expiration date of Pat. No. 5,330,974.

[21] Appl. No.: 225,853

[22] Filed: Apr. 8, 1994

Related U.S. Application Data

[62] Division of Ser. No. 24,121, Mar. 1, 1993, Pat. No. 5,330,974.

[51] Int. Cl.$^6$ ........................................ A61K 38/00
[52] U.S. Cl. ........................... 514/21; 530/382; 530/419; 530/421
[58] Field of Search ................. 514/12; 530/382, 530/421, 419

[56] References Cited

U.S. PATENT DOCUMENTS

| | | |
|---|---|---|
| 3,631,018 | 12/1971 | Shanbrom et al. . |
| 3,682,881 | 8/1972 | Fekete et al. . |
| 3,904,751 | 9/1975 | Zwisler et al. . |
| 3,931,399 | 1/1976 | Bohn et al. . |
| 4,177,188 | 12/1979 | Hansen . |
| 4,265,233 | 5/1981 | Sugitachi et al. . |
| 4,285,933 | 8/1981 | Fukushima et al. . |
| 4,297,344 | 10/1981 | Schwinn et al. . |
| 4,298,598 | 11/1981 | Schwarz et al. . |
| 4,359,049 | 11/1982 | Redl et al. . |
| 4,362,567 | 12/1982 | Schwarz et al. . |
| 4,377,572 | 3/1983 | Schwarz et al. . |
| 4,383,989 | 5/1983 | Rock . |
| 4,407,787 | 10/1983 | Stemberger . |
| 4,414,976 | 11/1983 | Schwarz et al. . |
| 4,427,650 | 1/1984 | Stroetmann . |
| 4,427,651 | 1/1984 | Stroetmann . |
| 4,442,655 | 4/1984 | Stroetmann . |
| 4,453,939 | 6/1984 | Zimmermann et al. . |
| 4,455,300 | 6/1984 | Wallace et al. . |
| 4,600,574 | 7/1986 | Lindner et al. . |
| 4,606,337 | 8/1986 | Zimmermann et al. . |
| 4,627,879 | 12/1986 | Rose et al. . |
| 4,631,055 | 12/1986 | Redl et al. . |
| 4,650,678 | 3/1987 | Fuhge et al. . |
| 4,650,858 | 3/1987 | Rasmussen et al. . |
| 4,655,211 | 4/1987 | Sakamoto et al. . |
| 4,672,969 | 6/1987 | Dew . |
| 4,676,790 | 6/1987 | Kern . |
| 4,683,142 | 7/1987 | Zimmermann et al. . |
| 4,690,684 | 9/1987 | McGreevy et al. . |
| 4,739,039 | 4/1988 | Vasquez et al. . |
| 4,770,176 | 9/1988 | McGreevy et al. . |
| 4,816,251 | 3/1989 | Seelich . |
| 4,818,291 | 4/1989 | Iwatsuki et al. . |
| 4,837,379 | 6/1989 | Weinberg . |
| 4,854,320 | 8/1989 | Dew et al. . |
| 4,874,368 | 10/1989 | Miller et al. . |
| 4,889,120 | 12/1989 | Gordon . |
| 4,902,281 | 2/1990 | Avoy . |
| 4,928,603 | 5/1990 | Rose et al. . |
| 5,002,051 | 3/1991 | Dew et al. . |
| 5,030,215 | 7/1991 | Morse et al. . |
| 5,330,974 | 7/1994 | Pines et al. ............... 514/21 |

*Primary Examiner*—Elizabeth C. Weimar
*Assistant Examiner*—Anish Gupta
*Attorney, Agent, or Firm*—Kenyon & Kenyon

[57] ABSTRACT

A therapeutic composition effective on contact with thrombin at a site of treatment in a patient as a tissue adhesive, hemostat or sealant, said composition comprising non-autologous, non-single donor mammalian fibrinogen that is capable of polymerizing when provided in solution at said site at a concentration of about 30 mg/ml thereof or less, to a fibrin network having therapeutically effective strength, wherein said composition contains less than about 30% (w/w), based on total protein mass present therein, of proteins other than fibrinogen, and further comprises a sufficient amount of one or more low molecular weight physiologically-compatible solutes such that said composition, if formulated as a lyophilized material, can be reconstituted therefrom at room temperature in sterile water for injection in about 30 minutes or less, at about 25 mg/ml of said fibrinogen. Additionally, methods for producing and maintaining said composition, and methods for the use thereof.

1 Claim, No Drawings

THERAPEUTIC FIBRINOGEN COMPOSITIONS

The present application is a divisional application of Ser. No. 08/024,121, filed Mar. 1, 1993, and allowed as U.S. Pat. No. 5,330,974.

FIELD OF THE INVENTION

This invention relates to therapeutic compositions comprising non-autologous non-single donor fibrinogen. More particularly, the invention is directed to the provision of a fibrinogen-containing composition effective as a tissue adhesive, hemostat, or sealant.

REPORTED DEVELOPMENTS

There is a recognized need for therapeutic compositions of physiological origin that are effective as tissue adhesives, as tissue sealants, or as hemostatic agents. Although there are available well-known synthetic materials for such therapeutic use, disadvantages have been identified with the use thereof. For example, the use of cyanoacrylate glue following surgery as a sealant or adhesive has been determined to cause toxic effects in tissues contacted therewith resulting in tissue necrosis and foreign body immune reactions. See, for example, Epstein, G. H. et al., *Ann. Otol. Rhinol. Laryngol.*, 95, 40–45 (1986). Similarly, the use of synthetic suture materials has been reported to result in tissue ischemia and necrosis.

It is known that therapeutic compositions for use as tissue adhesives, sealants or hemostatic agents can be made using the proteins fibrinogen and thrombin, Cronkite, E. P. et al., *J.A.M.A.*, 124, 976 (1944), Tidrick, R. T. and Warner, E. D., *Surgery*, 15, 90 (1944). Fibrinogen is a soluble protein found in the blood plasma of all vertebrates that when contacted by thrombin (another plasma protein) becomes polymerized to an insoluble gel-like network. In polymerized form, the fibrinogen is referred to as fibrin. The conversion of fibrinogen to fibrin is crucial to normal hemostatis in vertebrates.

There are numerous potential advantages, relative to the use of synthetic materials, associated with the use of fibrinogen as an adhesive, sealant or hemostatic agent. For example, when applied to a wound, polymerized fibrinogen (fibrin) forms a network or scaffolding through which it is more likely that immunologically active cells (to defend against invading pathogens) and also epithelial cells (for tissue regeneration and repair) can migrate. Additionally, fibrin materials may be dissolved gradually by the body (a process termed fibrinolysis) after treatment leading to more normal appearance of the healed site.

By way of background, restriction of the flow of blood in response to a wound involves a complex series of physical steps and biochemical reactions that are divided broadly into two major processes, primary and secondary hemostasis. Primary hemostasis involves the formation of a soft clot composed primarily of platelets, non-nucleated blood cells approximately 5 microns in diameter. Primary hemostasis is accomplished when platelets attach to adhesive macromolecules exposed on damaged vascular endothelium.

Secondary hemostasis refers to the reinforcement of the soft platelet clot. This secondary process is initiated by coagulation factors, enzymes that circulate in the plasma in inactive form but that become activated during primary hemostasis. The sequential activation of these enzymes results ultimately in the production of the coagulation factor thrombin from its inactive precursor form known as prothrombin. Thrombin then acts to polymerize fibrinogen into the insoluble polymeric matrix known as fibrin. As described below, an additional protein factor, factor XIII, is involved in stabilizing the fibrin network. The fibrinogen molecule has a molecular weight of about 340,000 and is a rod or ellipsoid-shaped particle. It has been determined that fibrinogen, in circulating form, consists of a dimer of 2 identical units each consisting of 3 polypeptides known as A$\alpha$, B$\beta$, and $\gamma$. The polypeptides contain numerous binding sites important to the final assembly of the fibrin network. For a detailed review of fibrinogen structure see Blombäck, B., "Fibrinogen and Fibrin Formation and its Role in Fibrinolysis" Chapter 11, pp. 225–269, in Goldstein, J. ed., *Biotechnology of Blood,* Butterworth-Heinemann, Boston, Mass. 1991.

Although the use of fibrinogen as an adhesive is known, the physical or chemical properties (for example, solubility) of the protein limit substantially its use. As noted in U.S. Pat. No. 4,650,678, at Column 1 thereof, difficulty is encountered in reconstituting fibrinogen from lyophilized material (the form of fibrinogen preferred for long term storage for clinical use). The '678 patent discloses also that fibrinogen solutions, to be effective as adhesive compositions, are generally believed to require a concentration of clottable fibrinogen therein of about 80 mg/ml or more (which may then be diluted 1:1, for example, at the time of use and at the treatment site with thrombin solution).

Additional fibrinogen-containing adhesive compositions and methods for the preparation thereof are provided in U.S. Pat. Nos. 4,298,598, 4,362,567, 4,377,572, and No. 4,414,976. Therapeutic adhesive fibrinogen compositions disclosed therein are stated to require concentrations of fibrinogen of at least about 70 mg/ml (which may again be diluted 1:1 at the treatment site by contact with a thrombin-containing solution).

The present invention relates to fibrinogen-containing compositions that have surprising clinical (medical) utility as adhesives, sealants, or hemostatic agents, and that provide therapeutically effective strength at fibrinogen concentrations at the treatment site of, for example, only about 10 mg/ml. The more dilute and less viscous nature of the therapeutic compositions provided according to the practice of the present invention decreases substantially the time necessary to resuspend such compositions from the lyophilized form, an important advantage in, for example, the hospital emergency room. Filtration of the fibrinogen during processing is also facilitated. In preferred form the fibrinogen used in the therapeutic compositions of the invention is of non-human mammalian origin, eliminating risk of contamination of product with human viruses.

SUMMARY OF THE INVENTION

Broadly stated, this invention provides for a therapeutic fibrinogen composition effective as a tissue adhesive, hemostat, or sealant, and that is more effective, per concentration of fibrinogen contained therein, than presently available compositions. Accordingly, there is provided a therapeutic composition effective on contact with thrombin at a site of treatment in a patient as a tissue adhesive, hemostat or sealant, said composition comprising non-autologous, non-single donor mammalian fibrinogen that is capable of polymerizing when provided in solution at said site at a concentration of about 10 mg/ml thereof or less, to a fibrin network having therapeutically effective strength, and further comprising a sufficient amount of one or more physiologically-compatible solutes such that said composition, if formulated as a lyophilized material, can be reconstituted therefrom at room temperature in sterile water for injection in about 30 minutes or less, at about 25 mg/ml of said fibrinogen.

There is provided also a therapeutic composition effective on contact with thrombin at a site of treatment in a patient as a tissue adhesive, hemostat or sealant, said composition comprising non-autologous, non-single donor mammalian fibrinogen that is capable of polymerizing when provided in solution at said site at a concentration of about 30 mg/ml thereof or less, to a fibrin network having therapeutically effective strength, wherein said composition contains less than about 30% (w/w), based on total protein mass present therein, of proteins other than fibrinogen, and further comprises a sufficient amount of one or more low molecular weight physiologically-compatible solutes such that said composition, if formulated as a lyophilized material, can be reconstituted therefrom at room temperature in sterile water for injection in about 30 minutes or less, at about 25 mg/ml of said fibrinogen.

The fibrinogen-containing compositions of the invention, effective at low protein concentration, are of importance in a clinical setting as they are more rapidly resuspended from the lyophilized state such as, for example, for emergency use in a hospital.

Still another aspect of the invention provides a method for producing a therapeutic fibrinogen composition comprising three or more steps including at least the steps of:

(A) precipitating fibrinogen from a sample of mammalian blood plasma with polyethylene glycol 1000;

(B) resuspending said fibrinogen in solution; and (C) reprecipitating said fibrinogen with glycine;

wherein precipitation of said fibrinogen with polyethylene glycol is performed only once.

The yield of purified fibrinogen derived from samples of mammalian blood plasma according to this process is typically about 90% or greater.

There are provided also methods for inducing tissue adhesion or hemostasis in a mammalian patient, or sealing a tissue in said patient, at a site of treatment therein, comprising contacting said site with a therapeutically effective amount of a composition of the invention.

Additional embodiments of the invention and the clinical importance thereof are described in connection with the following detailed description of the invention.

DETAILED DESCRIPTION OF THE INVENTION

Introduction

This invention provides for fibrinogen-containing therapeutic compositions effective as tissue adhesives, tissue sealants or hemostatic agents. Although a therapeutic composition of the invention may perform only one of the above functions at a particular site of treatment in a patient, all the compositions retain, nonetheless, the capacity to perform all three of the aforementioned functions. Additionally, there are clinical (medical) indications, such as the treatment of burns, plastic or reconstructive surgery, tissue grafting, or the treatment of anastomotic sites for which the compositions may perform simultaneously two or even all three of the aforementioned functions, that is, as adhesive, sealant and hemostatic agent.

As described below, important aspects of the invention include new methods for the purification of fibrinogen suitable for the formulation of the aforementioned compositions, and methods for the use thereof.

The importance of the present development is based upon the discovery that fibrinogen compositions provided according to the practice of the invention possess greater adhesive strength than that of prior art compositions. Without being limited as to theory, it is likely that the particular combinations of steps in the fibrinogen purification procedures described below facilitate rapid isolation of samples of clottable fibrinogen containing therein only small amounts of irreversibly aggregated or inactive protein molecules. Additionally, fibrinogen produced according to the practice of the invention and prepared in lyophilized form, is provided in intimate contact with particular physiologically-compatible solutes (proteins and/or low molecular weight solutes), the presence of which stabilizes, and facilitates resuspension of, the fibrinogen.

As will be described in detail below, the novel compositions of the present invention have important clinical benefits. In particular, since only a low concentration of fibrinogen is contained therein, and said fibrinogen is of a soluble and clottable character, the compositions can be resuspended from the lyophilized state for clinical use very rapidly, thereby facilitating emergency treatments and/or minimizing the time needed to complete surgical procedures. Filtration of fibrinogen solutions during processing (such as through a 0.22 micron filter) is also facilitated thereby.

Additionally, and as described further below, although addition of solubilizing agents to fibrinogen compositions in order to facilitate the resuspension thereof has been described previously, most such agents (at least at the resultant concentrations thereof) are non-physiological, limiting the types of therapeutic treatments that may be performed with the resultant compositions at target tissue sites. For example, non-physiological concentrations of a salt in a fibrinogen adhesive may interfere, osmotically, with communication of vital tissue fluids between a grafted tissue and the graft bed. Accordingly, the presence in such compositions of high concentrations of solute sets a limit on the clinical utility thereof.

The therapeutic compositions of the invention comprise non-autologous, non-single donor mammalian fibrinogen, that is, they comprise fibrinogen derived (pooled) from multiple mammalian donors. Preferred donors are mammals other than the human. The preparation of autologous or of single donor human fibrinogen for use as an adhesive sealant or hemostatic agent is well known in the art. See, for example, Dresdale, A. et al., *Surgery*, 97(6), 750–754 (1985); Siedentop, K. H. et al., *Laryngoscope*, 95, 1074–1075 (1985); Epstein, G. H. et al., *Ann. Otol. Rhinol. Laryngol*, 95, 40–45 (1986). An advantage associated with autologous fibrinogen preparations is that use thereof obviates the concern for transmission of human viruses. Disadvantages associated with the use thereof include unpredictable adhesive strength, and that the product may be available only in limited quantities and not be available on demand. Additionally, in a clinical setting, emergency room personnel would need to be diverted to the production thereof at a time when available personnel may be limited.

Fibrinogen-based adhesives (fibrin glues) are accepted for therapeutic use in Europe. It is noted however that such compositions, if made from pooled human donor plasma, are not approved for therapeutic use in the United States because of the risk of transmission of viral disease such as AIDS and hepatitis B and C. Numerous incidents of infection have been reported. Accordingly, practitioners of the art have sought to provide the aforementioned autologous or single donor fibrinogen compositions to minimize also risk of viral infection. As aforementioned, there is however substantial variation in the fibrinogen content of such preparations owing to individual patient (donor) variability. Accordingly, a further disadvantage associated with the use of such preparations is the difficulty in predicting, accurately, the clinically effective dose thereof.

An alternate resolution to the above-mentioned risk of viral infection, characteristic of human plasma-derived therapeutic products, is to provide fibrinogen from a mammalian source other than from humans. Fibrinogen compositions that could be provided from mammalian species other than the human are disclosed, for example, in U.S. Pat. Nos. 4,377,572 and 4,362,567. However, the therapeutic compositions defined therein are stated to contain at least about 70 mg/ml or more of fibrinogen (prior to any dilution at the site of treatment) leading potentially to the presence also therein of a substantial amount of additional and antigenic protein impurities, there resulting an associated risk of severe immune response. For example, rejection of grafted tissue triggered by immune response to the adhesive used at the graft-host interface may be more likely to occur. Such immune responses are predicted to affect, most severely, patients requiring numerous repeated treatments such as, for example, in response to severe burn injury, scarring or wounding.

In contrast, a principal advantage of the therapeutic compositions of the present invention is that they provide therapeutically effective strength at a treatment site when the fibrinogen thereof comes to be present at a concentration of only about 10 mg/ml, or even lower. Additionally, up to about 95%, or greater, of the total protein present therein is fibrinogen. Accordingly, the likelihood of adverse immune response is minimized.

It is noted that fibrinogen itself has an amino acid sequence and also a tertiary structure that is conserved substantially between, for example, the cow and the human forms, so that by proper selection of a donor mammalian species, risk of potential antigenicity to a patient can be very significantly minimized. In this regard, alternate preferred sources of mammalian fibrinogen include swine, goats and horses.

Use of highly purified bovine fibrinogen compositions for the treatment of human patients is preferred, therefore, since the product may be applied, efficaciously, at a dose that presents to the patient's immune system very little foreign antigen (derived also from the total composition of other serum proteins). Additional advantages of the therapeutic compositions of the invention will be apparent from the following further discussion of the properties thereof.

Therapeutic compositions of the invention can be formulated as lyophilized materials, or in the form of solutions or as frozen solutions. It is most preferred, if long term storage of product is required, that the compositions be formulated as lyophilized materials. Storage in the form of frozen solutions is preferred also in which case storage at or below −20° C. is most preferred. Therapeutic compositions of the invention prepared in the form of aqueous solutions are best used within about 4 hours of being prepared in solution form.

In connection with administrating the therapeutic fibrinogen-containing compositions at a treatment site in a patient, the fibrinogen composition (typically a solution thereof reconstituted from the lyophilized state) is normally administered in conjunction with an additional thrombin-containing solution, there resulting dilution of the fibrinogen to a final lower concentration. Typical protocols in the art call for equal volumes of therapeutic fibrinogen-containing composition (as a solution) and of an additional thrombin composition (also typically a solution). The use of numerous fibrinogen-containing compositions known in the art has been stated to require the presence therein of a minimum of about 70 mg/ml of fibrinogen, there being derived therefrom, fibrinogen, of at least about 35 mg/ml, at the treatment site. The fibrinogen-containing therapeutic compositions of the present invention are effective, however, even when the final concentration of fibrinogen derived therefrom at the treatment site (taking into account the volume of any thrombin solution applied therewith) is only about 10 mg/ml or lower.

Therapeutic Compositions of the Invention

A characteristic and novel feature of the fibrinogen-containing therapeutic compositions of the invention is that from such compositions fibrinogen can be provided that is capable of polymerizing, at a site of treatment in a patient, at a concentration of about 30 mg/ml or less, to a fibrin network having therapeutically effective strength. Provided also according to the practice of the invention are therapeutic compositions wherein said therapeutic strength is achieved at a fibrinogen concentration of about 5 to about 10 mg/ml.

As described below the fibrinogen-containing compositions of the invention are mixed with an additional thrombin containing composition to provide, at the treatment site, a reactive therapeutic composition containing fibrinogen having the aforementioned efficacy. In connection with the use of the fibrinogen-containing therapeutic compositions of the invention, the following considerations are of note. The therapeutic compositions of the invention can of course be used to provide efficacious fibrinogen at a site of treatment in a patient wherein the concentration thereof is greater than about 30 mg/ml, as long as the fibrinogen so provided is effective (as measured by the procedure of Example 2) at below about 30 mg/ml. Additionally, the concentration (and therefore volume) of a fibrinogen-containing therapeutic composition can be adjusted to accommodate the concentration (and therefore volume) of the additional thrombin-containing composition to provide a volume of reactive therapeutic composition appropriate to the course of treatment and as the clinical practitioner selects.

Preferable in the practice of the invention are those fibrinogen-containing therapeutic compositions from which fibrinogen can be effectively provided, in solution, at a site of treatment in a patient at a final concentration of between about 7.5 mg/ml and about 25 mg/ml. Highly preferred are compositions from which fibrinogen can be so provided at a final concentration between about 10 mg/ml and about 20 mg/ml.

In connection with selecting an appropriate concentration of mammalian fibrinogen (for example, bovine fibrinogen) produced according to the practice of the invention for contact at the treatment site, the following factors are among those to be considered: (A) minimizing the concentration of fibrinogen will result also in limiting the amount of contaminating (bovine) plasma proteins that may cause an immune response in the patient, (B) minimizing the concentration of fibrinogen limits the time necessary to resuspend a lyophilized starting material, (C) minimizing the concentration of fibrinogen reduces the viscosity of the fibrinogen solution thereby improving delivery characteristics in a clinical setting, and (D) providing fibrinogen of the highest purity. Additionally, it is also necessary to provide sufficient therapeutically effective fibrinogen in a short period of time so that the polymerized fibrin so formed is of sufficient therapeutic strength.

For many clinical indications, contacting the treatment site with a solution of therapeutic composition providing fibrinogen at a resultant final concentration of about 10 mg/ml to about 20 mg/ml thereof is most appropriate. Routine experimentation, however, as is known in practice of the present art can be used to optimize an appropriate concentration (whether higher or lower) of fibrinogen for any particular clinical application. This may be accomplished by monitoring the treatment site to determine, for example, if hemostasis has been stably achieved, whether a graft has adhered properly, or whether site of anastomosis has been sealed. In the event the result is not yet satisfactory, additional composition may be applied accordingly to the methodology of the clinical art. It is important to note again that the clinical use of fibrinogen at a final concentration thereof that is higher than the concentrations referred to above in connection with describing the capabilities of fibrinogen compositions of the present invention is, nonetheless, within the practice of the invention if the fibrinogen, or therapeutic compositions containing same, express the appropriate properties that are used herein to define the fibrinogen-containing therapeutic compositions of the invention.

In the preferred practice of the invention, at least about 80% of the fibrinogen present in a therapeutic composition of the present invention will be clottable, that is, polymerizable to fibrin in the presence of thrombin. There are numerous reasons (such as denaturation) why at least a portion of the fibrinogen molecules derived from a purification process therefor may not be clottable. As described below (see Example 1) fibrinogen that is 90% clottable, or higher, is produced readily according to the practice of the invention.

However, and without being limited as to theory, it is believed that the residual amounts (and types) of blood plasma proteins that are present in the therapeutic compositions of the present invention stabilize fibrinogen, preserving its clottability and facilitating also resuspension thereof from the lyophilized form. As discussed in greater detail below, such blood plasma proteins are referred to in the practice of the invention as physiologically-compatible solutes.

Determination of the percent of fibrinogen contained in a sample that is clottable can be determined following, generally, any of several standard assay procedures. See, for example, Blombäck, B. and Blomäck, M., *Arkiv Kemi.,* 10, 415 (1956) and Jacobson, K., *Scand. J. Clin. Lab Invest.,* 7(Suppl. 14), 1 (1955). Clottability determinations were performed, according to the practice of the present invention, using the method described in Example 3 below.

The therapeutic compositions of the present invention contain a population of fibrinogen molecules that is capable of polymerizing when provided in solution at a site of treatment in a patient at a concentration of about 30 mg/ml thereof or less, to a fibrin network having therapeutically effective strength. The term "therapeutically effective strength" is defined specially herein, according to the methodology of Example 2 below, to mean that a liquid sample of the therapeutic fibrinogen-containing composition provided for testing (as 0.8 ml of a 20 to 21 mg/ml fibrinogen solution prepared by reconstition from a lyophilized powder) demonstrates an average adhesive strength of at least about 900 grams, based on multiple trials. Therapeutic compositions preferred according to the practice of the invention have average adhesive (breaking) strengths, based on multiple trials according to the procedure of Example 2, of at least about 1100 grams, with an average of at least about 1200 grams, or higher, being most preferred.

Example 2 below makes reference also to numerous other testing procedures that have been used in the art to test, perpendicularly, horizontally or at an intermediate angle, the effective strength of fibrin networks. Although the absolute value of the adhesive strength of the therapeutic compositions of the present invention will vary, as will that of the prior art compositions depending, necessarily, on the specific test procedure employed, the relative values of adhesive strength of the compositions of the invention, in relation to those of the prior art, per equivalent amount of fibrinogen per sample, are substantially maintained.

As aforementioned, it is preferred that at least about 80% of the fibrinogen in the therapeutic compositions of the invention be clottable. It is preferred also that the compositions contain less than about 30% (w/w) based on total protein mass present therein, of proteins other than fibrinogen. According to the practice of the invention (see Example 1 below), purification of fibrinogen may leave in contact therewith amounts of other protein species, notably serum albumin, gamma globulin, plasminogen, plasma fibronectin, and also factor XIII. Preferably, therapeutic fibrinogen compositions within the practice of the invention comprise, as percent by weight of total protein contained therein, clottable fibrinogen of at least about 56%, about 14% or less of non-clottable fibrinogen, serum albumin at less than about 20%, gamma globulin at less than about 10%, plasminogen at less than about 1%, and plasma fibronectin at less than about 3%. The concentration of serum albumin is most preferably less than about 4 to 5%.

A highly preferred therapeutic composition which is produced routinely according to the process described in Example 1 below comprises (expressed as percent (w/w) of total protein contained therein) bovine fibrinogen at about 95%, and of which about 90% thereof is clottable; serum albumin at about 0.8%; gamma globulin at about 0.02%; plasma fibronectin at less than 0.5%; plasminogen at less than 0.02%; and also factor XIII at about 0.1 unit/mg fibrinogen.

Fibrinogen concentrations of up to about 95%, expressed as (w/w) of total protein, are achieved according to the process of Example 1 of the invention as described below.

The presence of coagulation factor XIII (fibrin-stabilizing factor) in the therapeutic compositions of the invention is highly preferred in that factor XIII acts to further stabilize the fibrin network with covalent crosslinking bonds. Preferred amounts of factor XIII in the compositions of the invention range from about 0.05 to about 0.2 units/mg fibrinogen. It is noted, however, that no special procedure need be followed in order that at least a sufficient amount of factor XIII be present in the therapeutic compositions of the invention, since sufficient factor XIII copurifies, invariably, with the product fibrinogen.

As described above, the therapeutic compositions of the invention contain fibrinogen molecules that provide therapeutically-effective adhesive strength at a fibrinogen concentration, at the treatment site, of only about 10 mg/ml. Without being limited as to theory, it is believed that the small quantities of the copurifying plasma proteins present, for example, in the highly preferred therapeutic composition defined directly above, are representative of a range of concentrations (preferably from about 1 to about 10%) of copurifying protein (expressed as % w/w of protein) that when present in conjunction with low molecular weight physiologically-compatible solutes (defined and described directly below) facilitate solubilization (reconstitution) of fibrinogen from the lyophilized state without interfering with the polymerization of the fibrinogen (fibrin) lattice. The below-described low molecular weight physiologically-compatible solutes are also effective in this regard when the total concentration of the copurifying plasma proteins is below about 1%.

In addition to the aforementioned copurifying proteins, the therapeutic compositions of the invention comprise also a sufficient amount of one or more low molecular weight physiologically-compatible solutes such that said resultant compositions, if formulated as lyophilized materials, can be reconstituted therefrom, at room temperature and in sterile water for injection, in about 30 minutes or less at a concentration of about 25 mg/ml of fibrinogen.

A low molecular weight physiologically-compatible solute, as defined functionally according to the practice of the invention, represents any solute of less than about 5000 daltons (preferrably less than about 1000 to 2000 daltons) that, at the particular concentration thereof in solution that is selected for use (or at a particular amount thereof present in a lyophilized fibrinogen-containing composition), facilitates reconstitution of fibrinogen as aforementioned, but does not interfere with the potential range of therapeutic functions of the fibrinogen composition so reconstituted. Additionally, a low molecular weight physiologically-compatible solute is one that is approved, or comes to be approved, by the United States Food and Drug Administration for use at the intended concentration, for clinical indications involving adhesives, sealants or hemostatic agents in humans. It is understood that a particular solute may qualify as physiologically compatible at one concentration (NaCl at 140 mM) but be incompatible at another concentration (for example, 1000 mM).

One example of how a low molecular weight solute can produce a physiologically incompatible effect has been mentioned, that is, by creating at the concentration thereof that is proposed to be used, an osmotic imbalance between a grafted tissue and a graft bed site interfering therefore with adhesion and/or healing at the site of treatment. Additionally, the substance may cause other deleterious effects at a treatment site, or at a site remote therefrom, such as to affect adversely wound healing, or to act as a barrier to physiological processes such as cell migration associated with tissue repair. The existence of such effects, for each potential solute, is well known in the art. Representative of solutes known to the biochemical art as effective solubilizing agents for fibrinogen protein but that are incompatible (at fibrinogen-solubilizing concentrations thereof) with clinical use are urea at about 500 mM or more; and sodium dodecyl sulfate at about 1% (w/v) or more.

Low molecular weight physiologically-compatible solutes representative of those which satisfy the functional criteria stated above include, at appropriate (fibrinogen-solubilizing) concentrations or amounts thereof, sodium chloride, sodium phosphate, the amino acids histidine, arginine, leucine and glycine, guanidine compounds, sodium citrate, and fatty acids. Concentrations (or amounts) of solutes that are appropriate to the practice of the invention may be determined for each particular solute by characterizing the properties of fibrinogen product (percent clottability, post-lyophilization stability and rate of solubilization) made according to the general protocol of Example 1.

Particularly preferred solutes that stabilize fibrinogen in lyophilized form, and that facilitate reconstitution therefrom, are sodium citrate incorporated into lyophilized fibrinogen-containing compositions at between about 0.10 mg and about 0.50 mg thereof per mg of fibrinogen; sodium phosphate similarly incorporated at between about 0.05 mg and about 0.5 mg per mg of fibrinogen; sodium chloride at between about 0.10 mg and about 1.0 mg per mg of fibrinogen; and epsilon-aminocaproic acid (added also as a fibrinolysis inhibitor) at between about 0.075 mg and about 1.0 mg per mg of fibrinogen. Other efficacious amounts of each of the aforementioned solutes, or of other solutes, whether present separately, or in combination, can be determined.

Example 1 below provides for the preparation of a highly preferred therapeutic fibrinogen composition that, in lyophilized form, contains a combination of the above low molecular weight solutes, in intimate contact with said fibrinogen, whereinby reconstitution of the therapeutic composition (at about 25 mg/ml of fibrinogen in 30 minutes or less, with sterile water for injection used as diluent at room temperature) is facilitated. Amounts of the above-identified solutes present in contact with the fibrinogen in the lyophilized preparation thereof were, approximately, and per mg of fibrinogen therein, 0.14 mg (NaCl), 0.12 mg (sodium phosphate), and 0.21 mg (sodium citrate), and 0.21 mg (epsilon-aminocaproic acid).

As described in detail below, the therapeutic compositions of the invention (including the lyophilized forms thereof for resuspension) are preferably formulated at (or for use at) a pH of about 6.5 to 8.5. Most preferably the pH of formulation is maintained at from about 7.5 to about 8.5.

Preparation of the Therapeutic Compositions of the Invention

The therapeutic compositions of the invention are prepared using a process that comprises, generally, the steps of (A) precipitating fibrinogen from mammalian blood plasma with polyethylene glycol 1000; and then (B) resuspending said fibrinogen in solution; and then (C) reprecipitating said fibrinogen with glycine; wherein precipitation of said fibrinogen with said polyethylene glycol was performed only once. More specifically, therapeutic fibrinogen-containing compositions of the invention were prepared following the procedure described in Example 1 below. Although the above-described effective methods are novel and nonobvious when viewed as a whole, individual steps thereof provide also important contributions to the clinical utility of fibrinogen product derived therefrom.

First, although samples of polyethylene glycol ("PEG") polymer having average molecular weights that vary through a wide range (including, for example, samples having average molecular weights of 5000 and 8000, "PEG-5000" and "PEG-8000" respectively) are useful in the practice of the invention, it is PEG 1000 that is preferred.

Precipitation of a pellet of fibrinogen with PEG-1000 (as specified according to the procedure of Example 1) leads to a cohesive fibrinogen precipitate that is more readily collected, for resuspension, than fibrinogen precipitate resulting from contact with, for example, PEG-8000. Accordingly, use of low molecular weight PEG (such as PEG-1000) facilitates recovery of clottable fibrinogen.

An additional advantage associated with the purification processes of the invention is that they are adaptable to the insertion of one or more additional steps, known in the art and approved in relation to the manufacture of clinical products, for the neutralization of mammalian viruses.

A further additional advantage that is derived according to the practice of the invention is that the substance epsilon-aminocaproic acid, added for its art-recognized role as fibrinolysis inhibitor, functions also as a low molecular weight physiologically-compatible solute that stabilizes fibrinogen, facilitating reconstitution thereof in therapeutically effective form from lyophilized material.

With respect to the use of low molecular weight physiologically-compatible solutes other than the species thereof utilized according to the specific procedure of Example 1 below, for the purpose of stabilizing fibrinogen and/or facilitating reconstitution thereof from the lyophilized form, appropriate solutions containing such solutes can be added (substituted) at particular points in the purification process such as, for example, when the fibrinogen, present as a glycine precipitate, is resuspended. Alternatively, the aforementioned fibrinogen precipitate may be resuspended with the buffer defined in Example 1, and then diafiltered against a solution containing other low molecular weight physiologically-compatible solutes useful in the practice of the invention.

Use of the Therapeutic Compositions of the Invention

The therapeutic compositions of the invention are useful in any of the clinical applications recognized in the art for which fibrinogen-based adhesives, sealants or hemostatic compositions can be used. In connection with the description of the invention herein, the terms adhesive, sealant, and hemostatic agent (hemostat) are defined broadly and used as these terms are understood in the art.

Tissue adhesion, sealing of tissue or hemostasis are induced in a mammalian patient at a site of treatment therein, according to the practice of the invention, by contacting the treatment site with a therapeutically effective amount of fibrinogen composition. According to the practice of the invention, such effective amounts need not be equivalent to amounts that cause complete or permanent adhesion of tissue, that effect, for example, total sealing of tissue boundary, or arrest completely bleeding or loss of tissue fluid from a tissue or tissue boundary. Rather, such compositions are within the scope of the invention, if the use thereof provides at least a partial effect that is of benefit to the patient in the course of a treatment.

The amount of sealant, hemostat or adhesive necessary to perform clinical procedures varies widely depending on, for example, the size of the treatment site in the patient, the nature of the condition in need of treatment and such factors as may be unique to each patient.

Additionally, in the context of many clinical applications, determination of an effective amount of therapeutic composition for use in connection therewith may depend on experimentation or "titration" of the treatment site with, for example, therapeutic samples that deliver increasing amounts of clottable fibrinogen to the treatment site. It is accepted in the art and well within the skill of clinical practitioners to determine for each patient and for each clinical indication, amounts (including, for example, volumes, concentrations, and number of any multiple layerings thereof that may come to be needed) of therapeutic fibrinogen composition that are effective.

The therapeutic compositions of the invention become effective, for use at a site of treatment in a patient, on contact with thrombin. Generally thrombin, at any effective amount thereof, may be provided to polymerize the fibrinogen of the compositions according to any method (whether generally or narrowly applicable) known to be effective in the art. Included therefore in the practice of the invention is the use of therapeutic fibrinogen compositions in which polymerization of the fibrinogen, in whole or part, is accomplished by endogenous thrombin, that is, thrombin of the patient that is or comes naturally to be present at the treatment site. Generally speaking, however, in the practice of the invention, thrombin is provided in the form of an additional composition, whether liquid or solid, (for example, see Example 2), provision of which is through any of numerous specific procedures that are, or may come to be, known in the art.

According to the practice of the invention, the aforementioned additional composition comprising thrombin is applied, usually, at the site of treatment in such a manner that from about 0.10 NIH unit up to about 1000 NIH units thereof are provided (preferably from a thrombin-containing solution) for each milliliter of fibrinogen-containing therapeutic composition utilized. However, greater or lesser amounts of thrombin may be used by the clinician depending on the circumstance of each patient according to good medical practice. Generally, it is preferred that from about 1.0 to about 300 NIH units of thrombin be provided for each milliliter of composition, however, the amount thereof may be varied according to the circumstance again following good medical practice.

The fibrinogen-containing therapeutic composition and the additional thrombin composition can be applied separately, or concurrently, to the site of the treatment, or they may be first combined and then applied rapidly (within a time frame generally known in the art or subject to determination by routine experimentation) to the site of treatment. In order that good mixing be achieved and for most clinical applications, it is preferred that the thrombin be applied to the treatment site concurrently with the fibrinogen solution, as a solution having a volume approximately equal to that of the said fibrinogen solution. It is within the practice of the invention to deliver the thrombin and fibrinogen-containing solutions at any combination of relative volumes, although certain combinations of volumes are likely, in most circumstances, to lead to the formation of less effective "reactive therapeutic compositions" as that term is defined below. For example, 1 µl of thrombin solution added to 2 ml of fibrinogen solution will likely lead to a composition of non-uniform strength due to time constraints on mixing and non-homogeneity of the formed matrix.

The thrombin and fibrinogen can be delivered to the treatment site through, for example, syringes including dual barrel syringes, or by other devices or means which allow for on-contact mixing. Examples of suitable delivery devices are described in U.S. Pat. Nos. 5,104,375, 4,359, 049, 4,631,055, and 4,874,368. Other of suitable delivery devices include pipettes.

The mixture formed from a fibrinogen-containing therapeutic composition and an additional thrombin composition define, according to the practice of the invention, a "reactive therapeutic composition" which contains, typically, and per milliliter thereof in contact with a site of treatment in a patient, between about 0.05 and 500 NIH units of thrombin and between about 7.5 and about 30 mg of fibrinogen. The selection of the particular concentration of fibrinogen and of thrombin present in a reactive therapeutic composition to be used in a particular clinical application, and for a particular patient, is guided by factors well known in the medical art including the size of the treatment site and the nature of the procedure to be effected. For example, if the fibrinogen-containing composition is used to effect rapid hemostasis at a large wound, it is generally appropriate to use a high concentration of thrombin in relation to fibrinogen (for example, about 500 units per ml of solution containing about 25 mg of fibrinogen) such that the fibrin clot is formed "immediately", that is, within seconds. Additionally, use of up to about 2000 to 3000 units of thrombin per ml of a fibrinogen-containing solution is known and is within the practice of the invention. However, if adhesion of a grafted tissue is being performed, wherein careful placement thereof and follow-up manipulation are required, a lower rate of polymerization may be effected using, for example, about 10 units of thrombin per ml of solution containing about 25 mg of fibrinogen.

In connection with the use of the therapeutic compositions of the invention, the following additional considerations are also noteworthy.

Lyophilized fibrinogen compositions of the invention can also be used directly in powder form as a sealant, adhesive or local hemostatic agent. If the lyophilized preparation is to be used in this fashion, it may be sprinkled directly, for example, onto a wound site or surgical incision where it reacts with endogenous thrombin to effect a seal or hemostasis. This is typically useful when the site (for example, a vessel or wound) to be closed is small, and blood loss is not rapid.

Additionally, the fibrinogen composition and/or thrombin may be applied, for example, to a wound or surgical incision by incorporation into a gauze pad, sponge, collagen or gel-type matrix or into a similar device and treating the area to initiate hemostasis or adhesion as necessary.

The fibrinogen-based compositions described herein afford a number of significant advantages over conventional surgical techniques (e.g., suturing) whether used alone as a means of surgical closure or used in combination with other techniques. The therapeutic compositions of the invention provide, potentially, a matrix for platelet adhesion and cell migration. Additionally, when the preparation is applied topically to an actively bleeding site, the fibrin matrix so formed may effectively trap platelets, triggering hemostasis-associated morphological changes in the platelets, and through a series of reactions involving both primary and secondary hemostasis, contribute further to effective clot formation.

Additionally, the fibrin matrix provides a compatible medium for the growth of contiguous cellular tissue. In this manner, cells from surrounding "like" tissue can infiltrate the matrix, promoting healing and facilitating replacement of damaged cells. The architecture of the affected tissue may therefore be restored substantially to that of the neighboring tissue by cells migrating from surrounding tissue sites. Similarly, production of scar tissue is minimized.

The therapeutic composition may be placed in any of pharmaceutically acceptable containers (such as packets, vials or bottles) depending on the intended clinical use. The containers may also be sized to accommodate small or large quantities of therapeutic composition depending upon the expected (or unexpected) needs of the physician. Preferably the containers are light resistant, and are stored also at or below about 5° C. prior to use.

Numerous of "inert" additives (substances such as preservatives, dispersants or additional diluents) known in the art can be added to the therapeutic compositions of the invention, with the understanding that such substances must be physiologically compatible as that term has been defined previously.

As aforementioned, the therapeutic compositions and methods defined by the present invention are useful in connection with any of the clinical applications where adhesives, sealants, and hemostatic agents can be used. In order that the clinical importance of the present invention be further illustrated, there follows hereafter mention of but some of the diverse clinical applications for which compositions and methods of the invention are very useful. Provision of high quality fibrinogen for use in conjunction with laser tissue welding, Oz, C. M. et al., *J. Vascular Surgery*, 11(5), 718–725, (1990); treatment and preservation of the ruptured spleen, Brands, W. et al., *World J. Surg.*, 6, 366–368, (1982); sealing of vascular protheses, Walterbusch, G. et al., *Thorac. cardiovasc. Surgeon*, 30, 234–235, (1982); sealing of vascular grafts prior to implantation, Kalmer, P. et al., *Thorac. cardiovasc. Surgeon*, 30, 230–231, (1982); sealing of microvascular anastomoses, Pearl, R. M. et al., *Surgery, Gynecology & Obstetrics*, 144, 227–230, (1977); for repair of middle ear defects, Epstein, G. H. et al., *Ann. Otol. Rhinol. Laryngol.*, 95, 40–45, (1986), and Silberstein, L. E. et al., *Transfusion*, 28(4), 319–321, (1988). A further important application includes bondings of a corneal inlay into a recess prepared to receive same in the cornea of a patient.

EXAMPLES

The following Examples are representative of the practice of the invention.

EXAMPLE 1

Preparation of a Lyophilized Fibrinogen Preparation Having High Capacity for Resuspension as Clottable Material Preparation of Solutions A fifty liter volume of bovine blood (obtained as about 10 liters each from 5 sacrificed animals) was collected into five ten-liter containers each containing 1.5 liter of anti-coagulant acid citrate dextrose solution, "ACD", USP Formula A, Baxter Health Care. The plasma fraction was separated by centrifugation at 3000 rpm (1700 g) for 20 minutes with the temperature held at 2°–8° C., according to standard practice.

A 67% solution (w/v) of polyethylene glycol was prepared by dissolving 670 gm of PEG-1000 (product P-3515, of Sigma Chemical Co., St. Louis, Mo., having mean molecular weight of about 1000 daltons) in sterile water for injection ("WFI") brought to 1 liter volume. A 3.33 molar solution of glycine was prepared by providing 250 g of glycine (Sigma Chemical Co., USP grade) in a 1000 ml beaker, brought to 1 liter volume with fibrinogen purification buffer as defined directly below (1 liter of the resultant glycine solution is required for each liter of plasma processed).

A fibrinogen purification buffer (hereinafter "buffer") was prepared as follows. Sodium chloride, 52.6 gm, for final concentration 150 mM; sodium citrate, 88.23 gm, for final concentration 50 mM; dibasic sodium phosphate, 42.59 gm, for final concentration 50 mM; and epsilon-aminocaproic acid "EACA" 78.71 gm, for final concentration 100 mM, were placed in a 6 liter Erlenmeyer flask and dissolved in 3 liters of WFI. 5M HCl or NaOH was then used to adjust the pH to 8.0, after which the volume was brought to 6.0 liters with additional WFI.

Purification Procedure

The following purification procedure, leading to product that is highly preferred according to the practice of the invention, was then carried out using aseptic technique as recognized in the art. ACD-treated bovine plasma (24.6 liters) was poured into a 55 liter Nalgene tank and stirred magnetically at a moderate speed so as not to cause foam to develop in the tank. A first precipitation of fibrinogen-containing material was commenced by adding slowly, and with continuous stirring, 4340 ml of the 67% (w/v) PEG-1000 solution over about a 5 minute period. At the end of the precipitation, plasma and precipitate were poured into sterile one liter polypropylene centrifuge bottles and capped. The samples were then centrifuged at 4000 rpm (2700 g) at a temperature of 2°–8° C. for five minutes.

The resultant supernatant was then decanted and the precipitate scraped aseptically from the bottles and placed into a 55 liter Nalgene tank. The empty bottles were then washed with buffer to recover as much of the remaining precipitate as practicable. A total of 8.2 liters of buffer was added, with the slurry resultant from the process having a final volume of ten liters. A magnetic bar was added to the flask to provide continuous stirring at moderate speed until the precipitate dissolved (about three hours).

A second precipitation was performed by adding continuously, over a 5 minute period with constant stirring, 25 liters of the aforementioned 3.33M glycine solution to the solution containing the redissolved precipitate. The resultant precipitate and solution were then transferred aseptically to one liter centrifuge bottles for centrifugation at 4000 rpm (2700 g), again at a temperature held to 2°–8° C. for five minutes. The resultant supernatant was then decanted and this second precipitate was transferred to a five liter Nalgene beaker. As much of the precipitate as practicable was removed by washing with a small amount of buffer. The recovered precipitate was then dissolved in 2.46 liters of buffer to yield a final solution volume of 3.5 liters.

The dissolved precipitate was then diluted further with 14 liters of WFI to provide fibrinogen in the solution at a concentration of about 5.7 mg/ml, as measured by a fibrometry assay, and the product solution was filtered (at 4–5 psi of nitrogen gas) through a 0.22 micron Sartobran PH filter, Sartorius Co. The resultant filtered volume was aliquoted to yield about 60 to 75 mg of fibrinogen per vial. For use in clinical practice, vials may contain such other amounts of fibrinogen as is appropriate for any of clinical indications for which such therapeutic materials are, or may be, used in the art.

The vials were then frozen at −45° C. over a period of about two hours time in a Revco Ultra-Low apparatus, and then lyophilized. Lyophilization was carried out as follows. Frozen vials were loaded in trays onto lyophilizer shelves. After cooling the shelves to about −50° C. (with product temperature brought to about −35° C.), the vials were then maintained at this temperature for about 3 hours. The chamber was evacuated to a pressure of about 300 milliTorr Hg, and shelf heating was initiated until, after a 16 hour period, the shelf temperature had reached about +38° C. (product temperature about −4° C.), and the chamber pressure had been decreased to about 200 milliTorr Hg. The temperature was held at (+)32° to 40° C. for about 24 hours, over which time the pressure was gradually decreased to about 75 milliTorr Hg. Vials were then stoppered and sealed. At least about 90% to 95% of the fibrinogen present in the sample of mammalian blood plasma subject to processing is typically recovered.

A representative analysis of the product derived from the above-described process was, as % (w/w) of total protein contained therein, fibrinogen 95%; serum albumin, 0.8%; gamma globulin, at 0.02%; plasma fibronectin, less than 0.5%; plasminogen, at less than 0.02%; and factor XIII, at about 1%, which equals an amount thereof such that if the lyophilized product were reconstituted to a solution having 20 to 25 mg/ml of fibrinogen, then the factor XIII would be present therein at about 0.1 unit/mg fibrinogen. Assays to determine the concentration of the copurifying proteins were performed as follows. For (bovine) fibrinogen, absorbance at 280 nm was determined based on a molar absorptivity of 1.55 ml/mg-cm at pH 7.0. Serum albumin, gamma globulin, plasma fibronectin, and plasminogen were each determined by ELISA methodology.

Factor XIII was determined by a functional assay based on the insolubility of crosslinked fibrin clot in dilute acid. One unit of factor XIII activity was defined as that present in 1 ml of normal citrated bovine plasma. See Simmons, A., Factor XIII Detection (Screening), in *Hematology, A Combined Theoretical and Technical Approach*, W. B. Saunders, Philadelphia, 1989, pp. 296–297.

epsilon-Aminocaproic acid was present in the final product lyophilized powder at about 13% (w/w), with fibrinogen making up about 59% (w/w) of the final weight of the product powder. The remaining weight percent of the product powder was provided by sodium chloride (about 9%), sodium citrate (about 12%), and sodium phosphate (about 7%).

Prior to use in adhesion testing (Example 2), the vial was reconstituted at room temperature with sterile water for injection (WFI) to yield a solution containing fibrinogen at 20–25 mg/ml, with about 90% thereof being clottable.

EXAMPLE 2

Determination of Therapeutically Effective Strength of Fibrin Networks

The following adhesion testing procedure involves determination of force (weight) necessary to detach a fibrin network sample from mammalian skin and is representative of the wide variety of similar procedures used by practitioners of the art. The procedure of this Example is adapted in part, and with modification, from the procedures of Burnouf-Radosevich, M. et al., *Vox. Sang.*, 55, 77–84 (1990) and Lindner, A. et al., *Wiener Klinische Wochenschrift*, 92 (suppl. 109), 1–9 (1980). Other recognized procedures that test adhesion strength in a perpendicular direction are described by U.S. Pat. No. 4,650,678; Wan, H. L. et al., *Transfusion*, 29, 41(s) (1989); and Marshall, *J. Urology*, 119, 310–311. Testing procedures based upon horizontal shearing or response to force at an angle are described by Saltz, R. et al., *Plastic and Reconstructive Surgery*, 88(6), 1005–1014 (1991), and by Siedentop, K. et al., *Laryngoscope*, 98, pp. 731–733 (1988) respectively.

Although use of different test procedures results, necessarily, in variation as to absolute amounts of adhesive strength measured (for example, weight held), the relative adhesive strength of particular fibrinogen compositions will be maintained through a series of such assays irrespective of the protocol employed.

For the present procedure, a section of full thickness skin (about 20 square inches) was removed from a laboratory guinea pig immediately after sacrifice. A scalpel was used to scrape excess fascia from the dermal side of the tissue. The testing procedure involves using 2 patches of skin each being about 2 inches square. The remaining portion of the skin sample can be frozen for future use. Prior to use, the skin patches were kept moist by wrapping in a damp sterilized cheesecloth impregnated with distilled water.

In order to perform the adhesion test, one piece of 2 inch square skin tissue was wrapped (dermal side out) around a brass contact plug having a 1 inch diameter and secured in place by a tightly wrapped nylon thread. The second square of skin tissue was secured (dermal side out) on a flat surface. A flat rubber O-ring, 1¼ inch I.D., was placed on the center of the second tissue square. The O-ring defines a confined space to be loaded with the fibrinogen test sample and also thrombin.

Accordingly, 0.8 ml of fibrinogen solution (prepared according to the procedure of Example 1 and reconstituted as described from the lyophilized powder prepared therein) was resuspended to a fibrinogen concentration of about 20 to 21 mg/ml (see below) using WFI. The thrombin solution was prepared by reconstituting lyophilized thrombin (Thrombostat® of Parke-Davis Co.) to about 10 units/ml in WFI. Equivalent thrombin is available as the following products, Thrombinar® of Jones Medical Co., and Thrombogen® of Gentrac Co.

While the O-ring was secured in place, 0.8 ml of the fibrinogen solution and 0.8 ml of the thrombin solution were delivered, simultaneously, to the center of the ring from separate syringes with thorough mixing.

The assay timer was started upon delivery of the two solutions. The skin-covered contact plug was then immediately placed into the ring where it was held gently in place for ten further seconds with care being taken to assure that the clot was not squeezed out of the ring. The contact plug was then allowed to stand on its own for 20 minutes anchored into the clot within the rubber ring.

Adhesion strength was measured by increasing, in 20-gram increments and at 30 second intervals, the weights placed in a cup attached to a string, the other end of which was attached to the contact plug (the weights are made to hang vertically by running the string through a pair of pulleys). In this particular version of the procedure, the first weight applied weighed 100 grams, with 30 second periods elapsing before the first of the 20 gram weights, and then the subsequent 20 gram weights, were applied. To prevent improper detachment, care was taken to support the weight bucket while each of the weights was added, the downward force on the polymerized composition being therefore relaxed and then reapplied following each addition of weight. The adhesive strength of the polymerized composition is reported herein as the value of the last weight held successfully, prior to breaking of the contact.

Fibrinogen purified, lyophilized, and reconstituted according to the procedure of Example 1 had a therapeutically effective strength (using 0.8 ml samples of fibrinogen solution, at about 20 to 21 mg/ml) of at least about 1100 to about 1200 grams based on multiple trials.

A single lyophilized fibrinogen preparation made according to the procedure of Example 1, was used to generate three separate resuspended (in WFI) samples having the following fibrinogen concentrations: Sample I (21.4 mg/ml), Sample II (20.2 mg/ml) and Sample III (20.1 mg/ml). Adhesive strengths measured by multiple trials (subsamples) for each of the samples were 880, 838, and 1154 gm (for Sample I); 660, 1150, >1218 and >1218 gm (for Sample II); and >1218, >1218, >1218, >1218 and >1218 gm (for Sample III). With respect to reported weight values that appear not to be even multiples of 20 gm, it was determined that some of the weights used had values (in grams) that were slightly different than 20 gm or a multiple thereof. The symbol >1218 (for greater than 1218 gm) indicates that the adhesive strength was found to be greater than the highest weight combination tested (1220 gm, which had an actual weight of 1218 gm).

The guinea pig skin samples can be used for subsequent runs if maintained moist in distilled water after being wiped free of residual clot material with, for example, a cheesecloth moistened with distilled water.

EXAMPLE 3

Determination of Clottable Fibrinogen

Clottable fibrinogen can be determined following generally any of several standard assay procedures such as Blomback, B. and Blombäck, M., *Arkiv Kemi.*, 10, 415–441, (1956) or Jacobsson, K. *Scand. J. Clin. Lab Invest.*, 7(Suppl. 14), 1, (1955). In the practice of the invention percent clottability was determined by taking advantage of the capability of a solution of thrombin (1 IU/ml, Sigma Chemical Co., St. Louis, Mo.) to polymerize fibrinogen with resultant loss of soluble absorbing material (at 280 nm) from the test samples.

Two ml fibrinogen test samples were adjusted (diluted or concentrated) to contain about 1 mg/ml of fibrinogen (containing therein unknown amounts of clottable versus inactive material) using the fibrometric procedure of Clauss, A., *Acta Haematologia*, 17, 237, (1957) to assay for total fibrinogen. This procedure is based on conversion of fibrinogen to fibrin in the presence of excess thrombin. The resultant normalized samples (2 ml) were mixed with 1 ml samples of thrombin (at 1 IU/ml). Samples were then incubated at 37° C. in a water bath for 30 minutes. Resultant clotted fibrin was removed by low speed centrifugation.

Appropriate control and blank solutions were also prepared consisting of: (A) unclotted fibrinogen, 2 ml of original undetermined sample at about 1 mg/ml total fibrinogen, and 1 ml buffer; (B) a thrombin zeroing blank (3 ml) containing 1 ml of the thrombin (1 IU/ml) solution, and 2 ml of assay buffer; and (C) a 3 ml blank of appropriate buffer for zeroing.

Percent clottability was defined as 100 times a fraction defined by the quantity [$A_{280}$ (unclotted fibrinogen) minus $A_{280}$ (corrected value)] divided by $A_{280}$ (unclotted fibrinogen), wherein the corrected value used therein represented the $A_{280}$ of fibrinogen remaining in the clotted supernatant corrected for (reduced by) the $A_{280}$ component contributed by the added thrombin.

We claim:

1. A method for producing a therapeutic fibrinogen composition comprising three or more steps including at least the steps of:

(A) precipitating fibrinogen from a sample of mammalian blood plasma with polyethylene glycol 1000;

(B) resuspending said fibrinogen in solution; and (C) reprecipitating said fibrinogen with glycine; and wherein recipitation of said fibrinogen with polyethylene glycol is performed only once and wherein at least about 90% of the fibrinogen in said sample is recovered.

* * * * *